United States Patent [19]

Graenicher et al.

[11] Patent Number: 5,269,469
[45] Date of Patent: Dec. 14, 1993

[54] METHOD FOR MEASURING THE FINENESS OR BULK DENSITY, APPARATUS FOR CARRYING OUT THE METHOD AND CONTROL SYSTEM WITH SUCH AN APPARATUS

[75] Inventors: Peter Graenicher, Flawil; Willy Braeker, Wil, both of Switzerland; Helmut Gemsjäger, Braunschweig, Fed. Rep. of Germany

[73] Assignee: Bühler AG, Uzwil, Switzerland

[21] Appl. No.: 954,869

[22] Filed: Sep. 30, 1992

Related U.S. Application Data

[63] Continuation of Ser. No. 771,731, Oct. 4, 1991, abandoned.

[30] Foreign Application Priority Data

Nov. 13, 1990 [DE] Fed. Rep. of Germany ....... 4036066

[51] Int. Cl.⁵ ................................................ B02B 5/00
[52] U.S. Cl. ........................................... 241/6; 241/37; 241/159
[58] Field of Search .................... 241/6, 9, 36, 37, 159

[56] References Cited

U.S. PATENT DOCUMENTS 2,392,636  1/1946  Boehler .
3,468,488  9/1969  Karrer et al. .
3,716,196  2/1973  Motek et al. .
4,881,689  11/1989  Lippuner et al. .

FOREIGN PATENT DOCUMENTS 1129735   5/1962   Fed. Rep. of Germany .
1598471   1/1972   Fed. Rep. of Germany .
  66126   5/1975   Fed. Rep. of Germany .
  66127   4/1977   Fed. Rep. of Germany .
3519625   9/1986   Fed. Rep. of Germany .
3623833   1/1987   Fed. Rep. of Germany .
 438760  12/1967   Switzerland .
1166332  10/1969   United Kingdom .

Primary Examiner—Douglas D. Watts
Attorney, Agent, or Firm—Martin A. Farber

[57] ABSTRACT

The fineness of bulk material, particularly of material to be ground, is determined by means of a flow measurement (DIN 66126) and by using a calibration correlation between medium particle size and permeability of the sample.

The medium fineness of a continuous flow of bulk material determined in such a way at predetermined intervals of time may be used for adjusting roll mill parameters. In the same way, it is possible to calculate the bulk density, so that a compacting procedure subsequently to a milling procedure can be adjusted accordingly.

36 Claims, 6 Drawing Sheets

METHOD FOR MEASURING THE FINENESS OR BULK DENSITY, APPARATUS FOR CARRYING OUT THE METHOD AND CONTROL SYSTEM WITH SUCH AN APPARATUS

CROSS-REFERENCE TO RELATED APPLICATION

This application is a continuation of Ser. No. 07/271,731 filed Oct. 4, 1991 now abandoned.

FIELD OF THE INVENTION

The invention concerns a method for measuring the medium fineness of bulk material, in particular of material to be ground, as well as apparatus for carrying out and applying this method.

BACKGROUND OF THE INVENTION

In rolling mills for grinding bulk materials it is known to adjust the grinding gap. This grinding gap determines, among other things, the maximum particle size of the bulk material that is passed between two rolls. It is to be understood, however, that below this maximum size the most diverse particle sizes will be possible, even though in general a relatively narrow particle size spectrum is aimed at. Such a control of a roll mill is described in U.S. Pat. No. 3,468,488, by way of example.

From U.S. Pat. No. 3,716,196 it is also known to regulate hammer mill in such a way that the product is thereafter subjected to a simple screening with a subsequent determination of the share of the oversizes. Further, in this case a maximum particle size is also given by the mesh size of the sieve, whereas the smaller particle sizes will not be taken into consideration for the control.

Finally, CH-PS 438 760 may be mentioned from which it is known to measure the size of gaps (but not of solid bodies) in a pneumatic manner.

Even if one came to realize that also the determination of the smaller particle sizes is important for a lot of processes, this would generally be determined by way of multiple sievings, which is a time-consuming process.

SUMMARY OF THE INVENTION

According to a first aspect, it is an object of the invention to provide a fast-working method for determining the particle size, in particular the average particle size (within the scope of this invention, the term "fineness" will mostly be used so as to avoid confusions with the particle size distribution, which os often referred to as "particle size" in the technical jargon).

This is accomplished in accordance with the invention by subjecting the bulk material to a measurement of its permeability by means of an apparatus measuring the permeability, thereby determining the flow resistance of the bulk material, or the pressure drop within the same, respectively, and deriving therefrom the medium fineness.

A further object of the invention is to provide a method by means of which a repeated, automatic, measuring of the medium fineness at predetermined time intervals will be made possible, in order to supply the measured values to a control device for the roll mill parameters, if so desired.

In accordance with the teachings of the invention, such a method comprises the following steps:

taking samples of a predetermined volume from a continuous flow of bulk material at predetermined time intervals;

forming samples of a substantially predetermined geometry, or of a geometry slightly deviating from this;

measuring flow parameters of the samples of bulk material by making a stream of gas flow through each of these samples;

derivation of the medium fineness of the bulk material from the flow parameters gained by the above method.

A still further object of the present invention is to provide an apparatus suited for carrying out the above-mentioned methods, or to use the bulk density for adjusting a grinding mill, respectively. According to the invention, such an apparatus comprises an installation for discontinuously taking samples of bulk material from a continuous flow of bulk material, a handling station for treating and/or transporting a sample holder to be filled with bulk material with a plurality of stations, of which one station is a filling station and another one a measuring station, as well as a station comprising a calculating unit whose function is to process the results determined in a measuring station in a predetermined manner so as to get a desired result.

Apparatus measuring the permeability as they are to be employed for the purposes of the invention, are described in DIN 66126, by way of example, which deals with the measuring principle according to Lea and Nurse, or according to Blaine. In accordance with the above-mentioned DIN-standard, the specific surface of powdery substances can thereby be measured. The invention is based on the realization that the specific surface would have to bear a particular ratio to the particles size, and that, therefore, it should be possible to determine the fineness of a sample of the bulk material with the help of such known devices. For example, this may be done by measuring—simultaneously with the sample to be measured—a reference sample, of which the average particle size is known, so that, by drawing a simple conclusion, the particle size of the sample to be measured can be determined. It is preferred, however, to perform the method in such a manner that first a comparison measurement of the average particle size and the flow resistance of a sample is carried out, whereupon a calculation of the correlation is made on the basis of this comparison measurement, which calculation establishes the ratio of average particle size to flow resistance; finally, in the case of at least one further sample merely the flow resistance will be measured, whose value is determined with the help of the regression equation gained from the calculation of the correlation.

After conducting a series of tests, it has appeared that the correlations are essentially linear and that, therefore, a linear regression of the form $$y = m \cdot x + b$$

will suffice for calculating the particle size. In principle, the first reference measurement for gaining the factor m and an add value b specific to a product must be carried out only once, whereupon these values may always be used for further measurements of a comparable bulk material. In view of this, the first step need not alway be carried out.

It has already been mentioned that the grinding gap of a mill, in particular of a roll mill with at least two grinding parts movable relatively to each other, determines only the maximum particle size, but not the average particle size. Nonetheless, with an appropriate method as described above, it will be possible to determine also the grinding gap, for only a reference-or calibration measurement is required to gain a factor m which, when multiplied with the respective flow resistance, or when adding the value b if another sample is measured, determines the maximum particle size and thus, indirectly, the desired grinding gap.

Now, even in the case of a mill of the type mentioned, this may be used for designing an arrangement in which, subsequently to this mill, a sample is provided, succeeded by an apparatus measuring the permeability, whose measured value corresponding to the flow resistance is fed to a control unit for the mill. When comminuting material according to the choke-feeding method (vide A. F. Taggart: "Handbook of mineral dressing", 1945, pages 4-73), various installations and parameters are known for the control of the mill, such as speed of the feeding installation, speed of the rolls, or adjustment of the grinding pressure. It is preferred, however, to use an arrangement in which a control unit adjusts a distance regulating unit for the grinding parts movable relatively to each other, such as grinding rolls in particular.

BRIEF DESCRIPTION OF THE DRAWINGS

Other characteristics of the invention will result from the following description and the embodiments schematically shown in the drawings, in which.

DETAILED DESCRIPTION OF THE DRAWINGS

Figure 2:
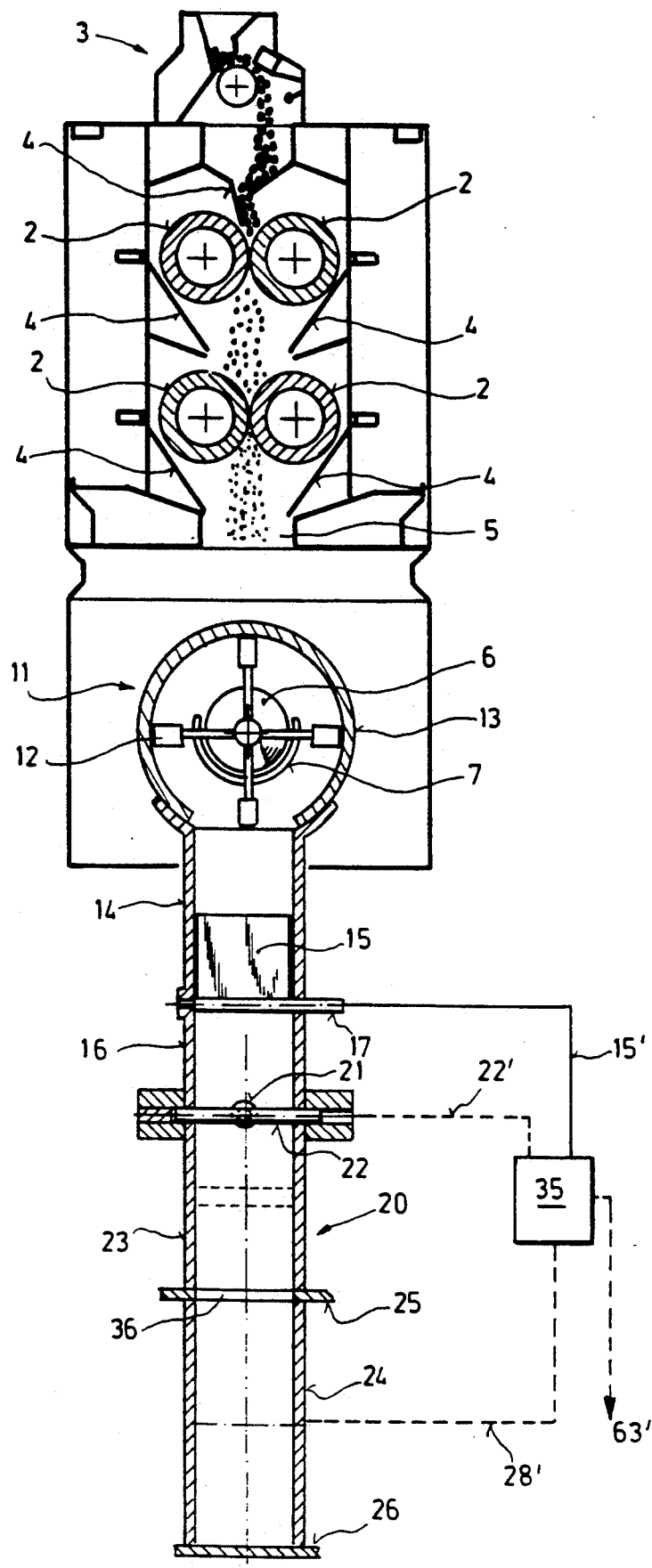
FIG. 2 represents a section along the line II—II of FIG. 1.

A roll mill 1 is designed for the dry grinding of bulk material, in particular of a material that is relatively brittle or embrittled, e.g. of roasted foodstuffs, such as coffee. For this purpose, it comprises a pair, preferably at least two pairs, of rolls 2. As illustrated by FIG. 2, a bulk material is supplied via a feeding installation 3 directly into the grinding gap of the first pair of rolls 2 pregrinding the bulk material, and thereafter to a second pair of rolls 2, with feeding surfaces 4 serving to make the dry bulk material pass to the respective grinding gap lying below or into an outlet 5, respectively.

Below the outlet 5 there is arranged a collecting screw conveyor 6 in a groove-shaped screw casing 7, which collecting screw conveyor 6 is illustrated best by FIG. 1. While the pairs of rolls 1 are each assigned their own drives 8 and 9, the collecting screw conveyor 6 comprises a separated motor 10 driving the spiral conveyor 6 via a step-down gear (now shown).

Figure 1:
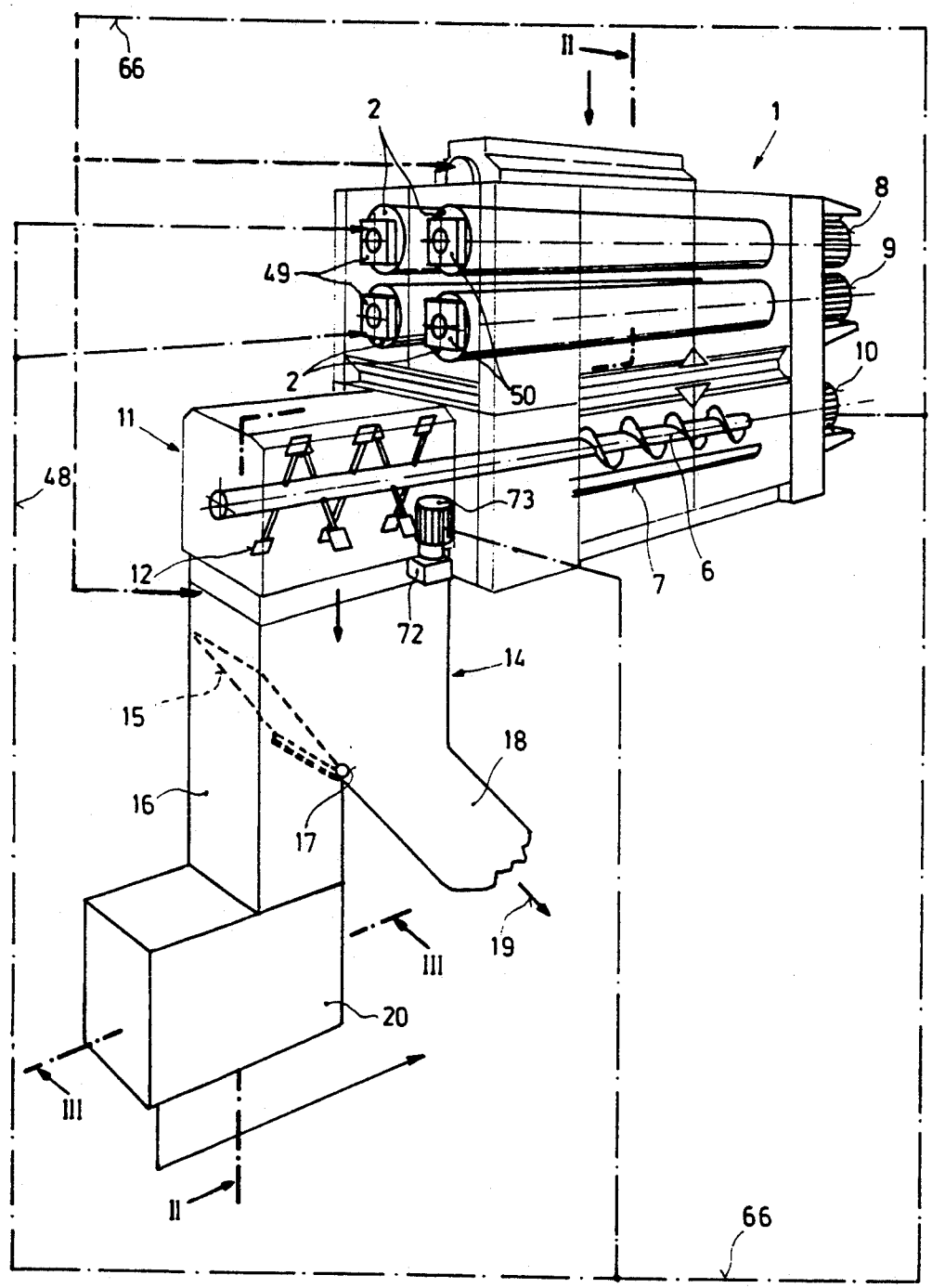
FIG. 1 shows a perspective view of a mill provided with a measuring apparatus in accordance with the invention for its control, of which mill

FIG. 1 further shows a homogenizing and compacting unit 11 arranged in a housing of its own, coaxial to spiral conveyor 6, which housing is provided with paddle arms 12 extending from it substantially in a radial way for intermixing the bulk material and varying or increasing its density. This homogenizing and compacting unit 11 serves to discharge the ground product, it being understood that the construction below the rolls 2 may be designed by any form although the intermixing and the variation of the bulk density is particularly advantageous for the intended measurement of the average fineness, but also for a desired determination of the bulk density. It may be mentioned, however, that instead of the tools shown—for example for application subsequently to a comminution according to the choke-feeding method—also reducing tools for reducing agglomerates generally arising in the course of that comminution by choke-feeding may be provided.

As is apparent particularly from FIG. 2, the compacting unit 11 is located in a housing enclosing the paddle arms 12 in a relatively tight way. To this housing 13 is connected at its bottom sie a conveying pipe 14 represented schematically in FIG. 1, or a hopper creating the connection from a square cross-sectional form to a round one. A sampler line normally closed by a flap 15 branches off from this conveying pipe 14. Flap 15 (or another sampler in place of it) is swiveled about an axis 17, which flap 15 is pivotable at timed intervals over an actuating appliance (now shown) in such a way that the conveying pipe section 16 is uncovered. Thus, while normally the completely ground material is fed to a storage bin, a bag-packing station, or a conveyor, via a conveying pipe section 18 running in the direction of arrow 19, a part of the material leaving the homogenizing unit 11 will fall into the sampler shaft 16 at a respective position of flap 15. In general, flap 15 will be actuated at regular intervals of time via a timing element, but for a lot of applications it may be preferred to use a random generatory by means of which flap 15 is actuated at irregular intervals.

Figure 3:
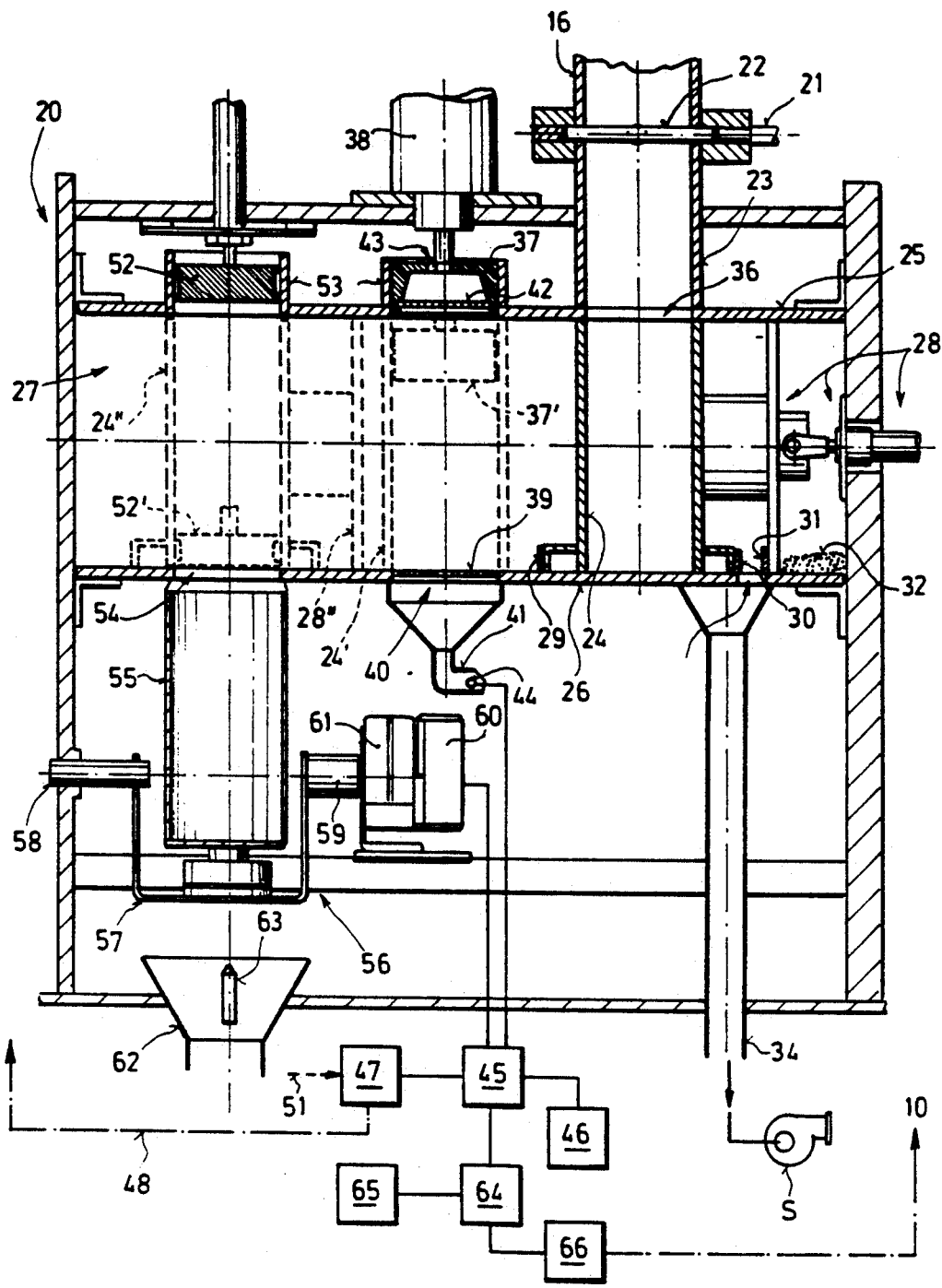
FIG. 3 illustrates the measuring apparatus in greater detail in a cross-sectional view along the line III—III of FIG. 1, whereas on the basis of FIGS. 4a to 4c three modifications for the adjustment of the bulk density are explained, with FIG. 4a representing an enlarged section across the compacting unit, similar to the cross-sectional design of FIG. 2, and with FIGS. 4b and 4c showing two embodiments of an actuation of flaps at the outlet of the compacting unit in a partial longitudinal section.

To the sampler section 16 is connected the housing of a measuring apparatus 20 whose details are represented in FIGS. 2 and 3. Accordingly, the measuring unit 20 is flanged to conveying pipe section 16 with a shut-off slider 22 operable via a rod 21 possibly being provided inbetween. As will be explained below, this shut-off slider 22 will ensure that the sample material will always fall from a predetermined height of fall onto a sampler holder 24 located below a connection piece 23 arranged within housing 20 and flanged to conveying pipe section 16.

The sample holder 24 can be displaced along the bottom 26 within a displacement area 27 limited by a cover plate 25 and a base plate 26 into three different positions illustrated in broken lines, with the help of a slider 28 drivable, for example, by a fluidic drive (not shown) or by the worm drive of a motor.

Preferably, the sample holder 24 comprises, at its bottom side facing bottom 26, at least one stripping edge 29, or 30, respectively, by means of which particles of the bulk material to be measured, fallen through apertures that are difficult to seal off onto the upper side of bottom 26, may be shoved aside so as to avoid frictional troubles. Also slider 28 may be provided with a stripping edge on that side facing bottom 26 even though, theoretically, it is also possible to make the wall of the slider end at such a distance from bottom 26 that a slot-shaped aperture will result above the bottom.

By means of these stripping edges 29 to 31 any bulk material is shoved aside (and toward pipe 34, if desired), as is apparent from the small piles of bulk material 32 represented schematically. It is preferred, however, to provide an aperture 33 on bottom 26 within the limits of at least one end region of such a stripping edge (in this connection, stripping edge 30), to which aperture 33 at least one line 34 ending in housing 20, and for example leading toward carrying-off unit 19 (FIG. 1), as well as a suction unit s, is connected, if required. By using such an arrangement it will no longer necessary to carry out a periodic cleaning for removing the small piles 32 because conveying line 34 with its orifice 33 in bottom 26 will allow a self-cleaning. It is evident that also at those places at which the small piles 32 are represented, cleansing pipes corresponding to line 34 may be provided.

As stated above, flap 15 (FIG. 2) may be controlled in a time-dependent way. To this end, a program control unit 35 may be disposed, controlling the motions of the individual parts via corresponding exits 15', 22', and 28' for actuating flap 15, shut-of slider 22 and slider 28 at respective time intervals. In this way, flap 15 will first be opened for a short time so as to by-pass a partial stream from line 14 into sample line 16. As soon as flap 15 has closed branch line 16 again, the shut-off slider 22 will be opened again, so that the volume of particles lying on it falls into sample holder 24. It may appear convenient to select the opening time for flap 15 in such a way that sample holder 24 will not be overcharged. However, in order to ensure that sample holder 24 may be filled completely, this period of time will preferably be chosen such that sample holder 24 will alway be overcharged, with the stripping edges 29 to 31 being provided for removing the excess. Moreover, it is to be understood that an aperture 36 will be provided in cover plate 25 at the level of the stationary connection piece 23.

As soon as this has happened, slider 28 will be operated, displacing sample holder 24 into position 24' as represented in broken lines. At the station corresponding to position 24', the actual measurement in the sense of DIN 66126 will be carried out, that is to say, the sample of bulk material will be compressed under a predetermined pressure within sample holder 24. For this purpose, a piston at a position 24' will be provided at the upper side of sample holder 24, which piston is movable via a cylinder aggregate into its lowered position 37' under the predetermined pressure, so that the sample of bulk material will be compressed in a predetermined way under this predetermined pressure.

According to DIN 66126, the sample must then be flown through by a gas of a predetermined volume per time unit, in order to measure the permeability, or the flow resistance, respectively (as a modification, a continuously constant gas volume may be conceivable). In principle, this would be possible at a position deviating from position 24', corresponding to a further motional step, but the measuring apparatus may also be designed in the manner represented, with an aperture 40 in bottom 26 covered by a sieve 39 being provided. The sieve 39 has a mesh aperture that is small enough to oppose the pressure of piston 37, thereby not allowing the particles of the sample to pass through.

Connected to this aperture 40, there is provided a gas supply unit 41, in particular for air supply, so that the sample located in sample holder 24 may be flow through. In principle, also an arrangement may be chosen in which, in place of sieve 39, a shut-off slider is provided, which will be opened when piston 37 has already compressed the sample ans has returned to its position represented in full lines (which, however, is not absolutely necessary), so that, by pulling away this shut-off slider, the aperture 40 for the gas supply will be uncovered. The piston 37 in turn conveniently also comprises a relatively close meshed sieve 42, whose meshes are small enough to ensure an effective pressure upon the sample, but large enough to allow the gas fed via supply line 41 and flowing through the sample to pass through. On the upper side of piston 37, at least one aperture 43 may be designed, through which aperture the air used for measuring the permeability may stream into the open, or else is passed off via a line not represented so as to be recirculated to line 41. As already mentioned above, it will also be possible to provide sieve 39, by way of example, or another covering (the above-mentioned slider) at another station, which, in such an arrangement, naturally need not comprise piston 37. In this case, piston 37 may be designed without the parts 42 and 43. Within line 41, a sensor is arranged at any position as such, measuring the pressure resistance of the sample contained in sample holder 24 and supplying a correspondent output signal to calculator 45, which receives the respective value for m and b from a transducer 46 and then supplies corresponding signals to a control unit 47. This may take place from a single transducer 46 by means of serial signals or via parallel lines, or else a respective separate transducer is provided for the two values m and b.

In addition, calculator 45 computes the bulk density from the known weight of sample holder 24 and the weight measured, which bulk density will be particularly important when the ground material is then to be poured into packings of a predetermined size and a predetermined filling weight. Also in this connection modifications would be conceivable for it would also be possible to make piston 37 compress the bulk material with a predetermined pressure, and then to determine the volume of the bulk material on the basis of the piston position (when using a piston-position sensor) or of a level sensor for the bulk level in sample holder 24 (which bulk level may be designed transparent for this purpose, by way of example, to enable an optical scanning).

Thus, a signal corresponding to the calculated actual value of the bulk density is supplied to a control stage 64 by way of a calculator 45, which control stage 64 receives a desired nominal value from an adjustable set-point adjuster 65. On the basis of these data, a control signal considering the deviation from the desired value is gained, which control signal is then fed to an adjusting stage 66. This adjusting stage 66 regulates the rotational speed of the compacting unit 11 and thereby its compacting pressure (if the compacting takes place with the help of other pressure-exerting installations, such as pressure pistons, or the like, the pressure of which will be regulated in an analog way).

The transducer 46 may be designed in the most diverse manner. In principle, it may be built according to the manner of station 24', in order to carry out—parallel to the measurement at station 24'—a comparison measurement, with this comparison measurement being derived from a standard sample of a known particle size. If, however, this step of calibrating is to be carried out manually, then transducer 46 may comprise only a simple input keyboard for the respective values of m and b for the maximum particle size (cf. the explanations referring to FIG. 3 in connection with FIGS. 5 and 6). It is be understood that, particularly when using the measuring apparatus without the mill 1, the respective values for the average particle size will be input via transducer 46. This may also be advantageous when grinding by choke-feeding. A further possibility is to design transducer 46 for the input of data determining the respective values for m and b. These data may include the kind of the product to be considered, such as roasted coffee, which gains a certain brittleness by the roasting treatment, or other material of a substantially brittle quality, such as concrete, coal or ore. Moreover, the force of pressure of piston 37 (if this is changeable), the sample length (if the sample holder 24 is not filled completely), the pressure prevailing in the line 41 (if this may vary) and in certain cases also the bulk density (if the load of piston 37 is changeable) may be input.

The output signal of the calculating stage 45, which practically represents a mere multiplication stage of a known design, is supplied to control unit 47, whose output line represented in dot-dash lines is also illustrated in FIG. 1. For if the calculated result of stage 45 corresponds to a desired value for the grinding gap, two procedures will be possible: either a position sensor is provided for determining the size of the grinding gap, e.g., for the relative position of movable roller bearings 49 relatively to rigidly mounted roller bearings 50, the output signal of which position sensor will then be fed as actual value to control unit 47 via a line 51 represented in broken lines in FIG. 3. Or else control unit 47 will work as a final control element (not shown) with an incremental system (for example with a stepping motor), in which case the respective position of the movable bearings 49 will be known to it. This may occur, for example, by making the rolls 2 move together—when starting the operation of mill work 1–until a grinding gap of "0" is reached so as to determine the zero point, whereupon they separate again until reaching a desired and adjusted grinding gap position. In this design, the control unit 47 will count either the steps of the stepping motor or the incremental steps of an incremental displacement pickup. But since the grinding rolls 2 frequently have a sensitive surface, it is preferred to choose the the contrary procedure by first having the rolls separate up to a defined open position, for example determined by a transducer or by a limit stop, and make them move together to a desired grinding gap position only then.

All these measures are known as such in control technique and therefore, need not be explained in more detail. On the contrary, it will be apparent that in this way, also when grinding dry materials, it will be easy to determine the average fineness and to readjust a mill aggregate accordingly. From U.S. Pat. No. 3,734,659 is known, for example, to influence the grinding gap, or the fineness of the material to be ground, respectively, by regulating the amount of material supplied by influencing the feed relatively to a given circumferential speed of the grinding rolls. Accordingly, the regulation of the speed of rolls at a given feeding speed will also be conceivable.

Therefore, if the sample contained in sample holder 24 has been measured already in position 24', it may be displaced to the next position of slider 28, to position 28', or to position 24' of sample holder 24, respectively, where an ejector piston 52 is guided in a similar cylindrical connection piece 53 as piston 37. This ejector piston travels through the whole sample holder 24 and reaches a position 52' at the end of its motion.

Now, in FIG. 3 there is provided and shown a possibility of correction. For when the measured bulk material has been pressed by ejection piston 52 from sample holder 24 in the position 24" through an aperture 54 of the bottom plate, then it can be shoved into a weighing receptacle 55 of scales 56. This weighing receptacle 55 is attached to a U-shaped bow 57 whose legs are mounted on stub shafts 58, 59. From these stub shafts 58, 59 at least one is connected to a pressure cell 60 by means of which the weight of a sample can be determined. Although with a completely filled sample holder 24 the weight would always have to be constant, slight differences may arise, which will then be fed as correction values from measuring apparatus 60 into calculating unit 45.

However, another procedure is conceivable too, for, on the one hand, piston 37 may be omitted, if one assumes that the height of fall—when filling sample holder 24—suffices to exert a predetermined pressure upon the material, thereby achieving a predetermined bulk density. It is true that for this height of fall the length of the socket piece 23 together with the sampler line 16 joining it and the line 14 lying above it may be used, but possibly too many interference factors will influence this procedure in a negative sensor, for which reason it will be advantageous to design shut-off slider 22 for the definition of the height of fall. Then, after having the sample flown through by air, which sample, in this design, has been compressed without the piston 37, but merely owing its own weight, a weighing procedure may start in receptacle 55, producing the necessary corrections. On the other hand, it will be understood that the weighing receptacle 55 along with scales 56 may also be dispensed with completely.

Immediately after finishing the weighing procedure, the stub shaft 59 will be turned by means of a drive 61 of any type known per se (moving-iron instrument, motor, electromagnet, fluidic motor), connected to the weight-measuring apparatus 60 with the respectable 55 getting into a position turned by 180°, whereupon its contents will be emptied into a hopper 62 conveniently leading to unit 10 (FIG. 1). If scales 56 are dispensed with, this hopper 62 would be arranged immediately below aperture 54. It will be advantageous—particularly in order not to distort the result of the weight-measuring procedure—to design a cleansing installation within the range of hopper 62 for the interior of weighing receptacle 55. Such a cleansing installation may be formed of a rotating brush, in principle, but it will be easier and more suitable to provide at least one fluid nozzle 63 for this purpose, in particular a compressed-air nozzle, whose compressed-air supply is for instance controlled by the program unit 35 (FIG. 2) via its exit line 63'.

It is to be understood that also with respect to the design and arrangement of scales 56 numerous modifications will be conceivable, such as the placing of the load cell 60 between the bottom side of receptacle 55 and bow 57, which, however, has the disadvantage that the supply lines must be made movable. Moreover, the measuring apparatus 20 for a linear displacement of sample holder 24 with the help of a slider 28 has been explained, which slider 28, which slider 28, after the ejection of the sample by means of piston 52, may, of course, return to its position represented in full lines; nevertheless, it would also be conceivable to design the individual stations 24, 24' and 24" along a circular path and to provide, in this case, instead of a linearly displaceable slider 28 a sort of turret construction rotatable about a drivable shaft relatively to which sample holder 24 is arranged eccentrically.

Figure 4A:
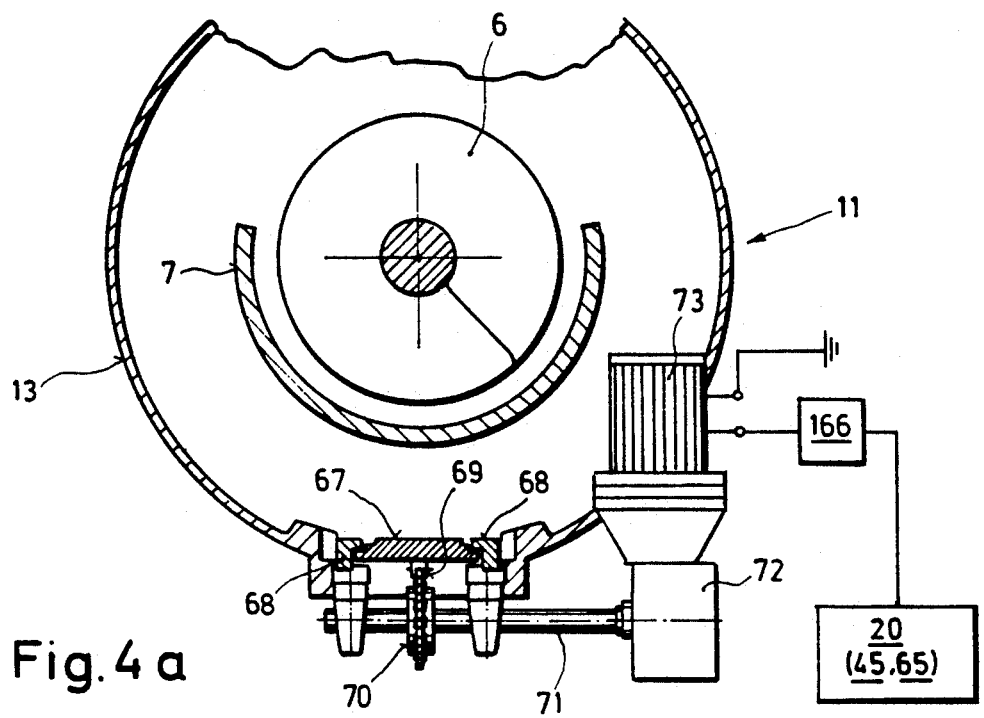
Figure 4B:
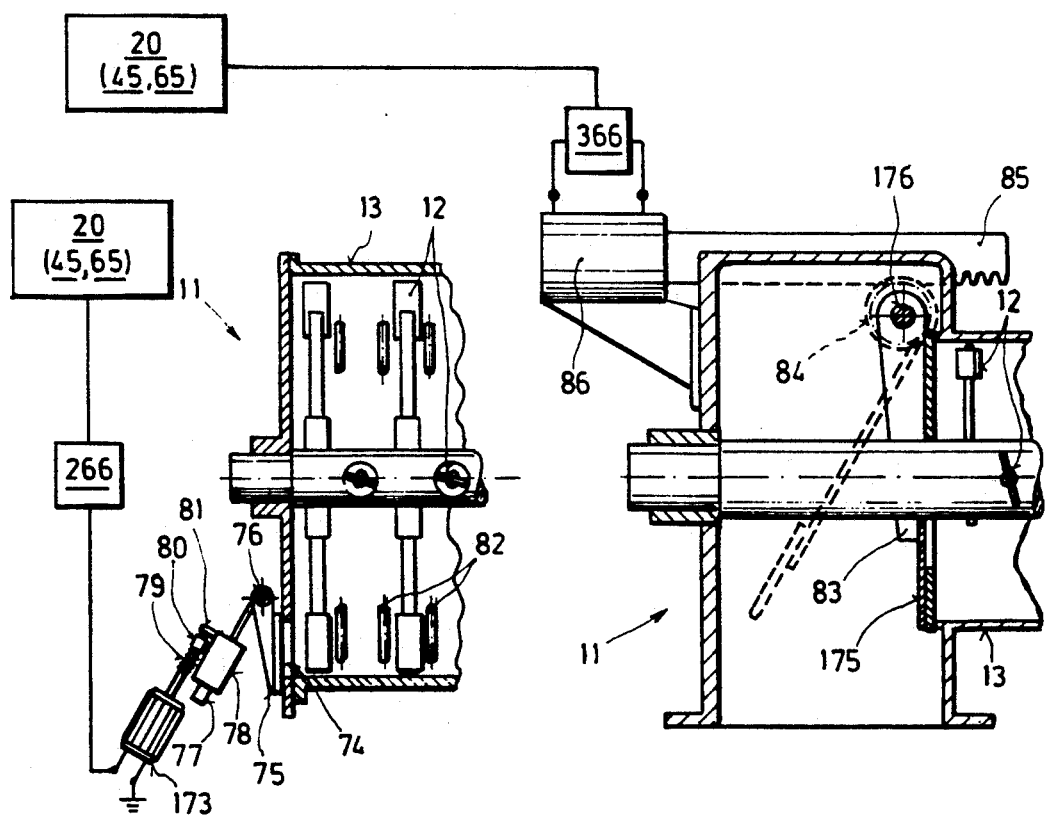
Figure 4C:
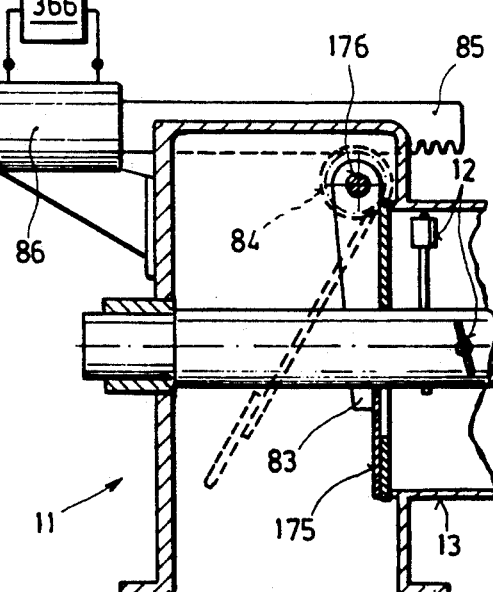

FIGS. 4a–c show three modifications being associated with each other by their common measuring apparatus 20, how the output signal of measuring apparatus 20 may be used in a different way as well. According to FIGS. 4a–c, the bottom side of the compacting housing 13 is closed by a slider 67 being displaceable in guiding rails 68, which slider 67 more or less closes the outlet of compacting unit 11. For its displacement, the slider 67 is connected at its bottom side to a chain 69 drivable via a chain wheel 70. In principle, this drive may also be effected by means of a toothed rack at slider 67 and a toothed wheel meshing with it (corresponding to wheel 70), but the chain drive is less sensitive and will therefore be preferred.

The wheel is mounted on a driving shaft 71 to which a rotational motion is imparted by a displacing motor 73 via a gear unit 72 (cf. also FIG. 1). For reasons of accuracy, it will be preferred to use a stepping motor as a displacing motor 73. This displacing motor 73 is controlled via an adjusting stage 166 functionally corresponding to adjusting stage 66 already described above, and which receives its control signal from the units 45 and 64.

In the case of FIG. 4b, however, the unit 20 is connected to an adjusting stage 266. In this arrangement, the compacting housing 13 has only a relatively small outlet opening 74 closed by a flap 75 swingable about an axis 76 and functioning as a counter-pressure member. This flap 75 is loaded by a weight adjustable along a lever 77. The position of this weight, and thus its pressure moment upon flap 75, is determined by the position of a limit stop 88 adjustable on a threaded spindle, said limit stop 80 cooperating with a counter stop on weight 78. The spindle 79 is connected to an adjusting motor 173, with the whole arrangement being similar to that described in a different context already in DE-A-38 39 778 for adjusting a weight.

Yet a construction similar to that shown by FIG. 4b may further be used for the following purpose: When, for example, an aperture leading downward and coverable by a slider 67 (FIG. 4a), as apparent, for instance in FIG. 1, is provided, then a (spring-loaded or) weighted flap 75 may additionally be provided at an aperture 74 so as to operate as relief flap in the case of a sudden clogging within housing 11. In this case, a control of the load of this flap may be omitted, however.

While in the case of FIG. 4b the compacting unit 11 comprises, additionally to the paddles 12, also stator tools 82 extending from housing 13, which stator tools 82 enhance a homogenization by the combing action with the paddles 12, such tools are missing in the case of FIG. 4c. In this arrangement, a larger flap 175 is attached to a lever 83 connected to a control shaft 176. At this control shaft 176, there is arranged a toothed wheel 84 represented in broken lines only with which a tooted rack 85 is meshing. This toothed rack 85 is actuated by a cylinder aggregate 86, which is controlled via a corresponding adjustment device 366, with the latter receiving its control signals from a control unit 64.

It will be understood that the adjustment of a discharge shutter unit 67, or 75 or 175, respectively, may be effected also additionally to the adjustment of the speed of the motor 10 driving compacting unit 11 (FIG. 1). For example, this may be accomplished according to the manner of a cascade control system by first operating one control system (e.g., the one of motor 10) and, when reaching the limits of the control range, the respectively other one (e.g., the one of the shutter unit). However, a faster response of the control system and thus a shorter control time constant due to the simultaneous response of the two control systems may be achieved as well.

It may be mentioned that the influencing of the compacting may be effected also by regulating the feed of the mill work correspondingly, as this is shown in FIG. 1 on the basis of the dot-dashed line 66 (exit of control stage 66). Yet this means a greater control time constant and will not be a preferred procedure, in general. Nevertheless, by way of exception, this control manner may be integrated into the cascade control system described above.

The invention is not limited at all to the measuring of relatively brittle particles, if required with subsequent adjustment of a grinding gap and/or the grinding pressure; on the contrary, also relatively fictile particles may be measured in this way. An example may be found in the manufacturing of flakes (e.g., ground oats, soybean flakes, etc.) on a squeezing or flaking mill. By subsequent measuring of the particle size and/or (preferred) of the bulk weight, conclusions may be drawn as to the average size of the flakes, and from this it will be established whether the determined size of the flakes lies within a desired range. On the basis of these data, corresponding control interventions for changing the pressure of the rolls, or their grinding gap, respectively, may be carried out.

In the following, the measuring of the particle size will be described in more detail. In principle, from the existing literature on this subject, two different kinds of apparatus are known with which the specific surface of the bulk material can be measured.

The so-called Blaine principle (DIN 66127) utilizes a method for flowing through the bulk material with a time-dependent pressure drop, and the Lea-and-Nurse apparatus with a temporally constant pressure drop.

Both principles of measurement serve to determine the specific surface of the bulk material, and the invention is based on the recognition that the specific surface is a function of the particle size, in particular, the medium one.

A measurement of a parameter determining the specific surface and its comparison with corresponding calibration values will result in the knowledge of the particle size.

In the interest of an automated measurement of the particle size during the fall for adjusting a mill work, it is, of course, not desirable to take a sample from time to time and to supply this to one of the above-mentioned apparatus so as to be measured by hand, to evaluate this measurement and to effect an appropriate adjustment of the mill work manually, but all these procedures are supposed to be carried out automatically.

Since the measurement of the specific surface of a bulk material in the two apparatus mentioned above presupposes an exactly predetermined fill geometry, which can be achieved only within certain limits when producing samples in an automatic way, it may be necessary to provide possibilities of correction, which will allow to compensate for the deviation of the rear sample geometry from the prescribed geometry.

For example, when applying the Blaine principle in the case of a given sample cross-section and height, the sample is to be compacted with a particular predetermined pressure so as to achieve a porosity representing the particle size. When compacting the sample by means of a piston in the measuring cylinder under the action of a predetermined force, a sample height is achieved which will not be constant, but rather depends on the particle size itself, and is dependent upon other parameters too, such as humidity of the air and the like, unless the quantity of sampling is changed for holding the volume constant, as provided according to Blaine.

Consequently, an arrangement must be chosen in which the real sample height can be determined, so that, in conjunction with the sample weight, it will be possible to calculate the porosity, which value may be used in the defining equation of the specific surface $$Sv = \frac{k}{(1 - \text{epsilon})} \cdot \sqrt{\frac{\text{epsilon}^3 \cdot t}{\text{eta}}}$$

In this equation, Sv stands for the specific surface per volume unit, epsilon designates the porosity, eta represents the viscosity of the air, and t is the value for the flow duration of a predetermined air volume through the bulk material. k is a proportional factor corresponding to the specific system geometry.

When carrying out a flow measurement, for example t, the duration of the flow through the sample by a predetermined air volume, will be established and, by way of the above equation, the specific surface, and from that the particle size, will be computed in a microprocessor. To this end, a calculation of Sv according to an equation and/or a determination of the particle size by comparing the specifice surface with the calibration curve takes place. The determination of the calibration curve occurs by means of flow measurements of samples carried out in an identical manner, the medium particle sizes of which are known, and which have been compressed by employing the same force and represent a predetermined sample height.

As stated above, the deviation of the real sample height from the prescribed height has to be compensated for, if required. This may take place after determining, in an mathematical way, the real sample height directly during the computation in the microprocessor, with the magnitude of the proportional factor being corrected proportionately. The real sample height can be measured, for example, by determining the path of the compressor piston, in which case the deviation of the real end position of the compression piston from its desired end position may be used as a correction value. The real end position of the compression piston can be determined by distance- or position measuring in a mechanical, electrical or optical way, by way of example. Of course, it will also be possible to directly measure the level of the sample cylinder after compression. In practice, a modification will be chosen which meets the other conditions, such as accuracy, speed and cost.

As described above, the FIGS. 1 to 3 show a measuring apparatus as provided by the invention, which is capable to fill sample cylinders at predermined time intervals, thereafter compressing them and supplying them to a measuring station in which a predetermined air volume is passed through the sample.

The equation indicated above applies to a measurement according to a Blaine procedure with varying pressure, and is to be understood here as example. Of course, the flow measurements may be carried out in another way too, for example, by taking into a account a constant pressure drop, in which case the amount of air per time unit will be determined, or else the pressure drip at a forced flow of a defined gas volume in a predetermined time is measured, for example according to the Lea-and-Nurse principle.

As stated above, this calibration curve may be established by way of a single reference measurement, if desired, since it has been proved that the ratio of flow resistance to particle size is a linear and proportional one in wide ranges. This will become apparent by the data in the following table which represents the measurements on the basis of four samples T12 to T15.

Figure 5:
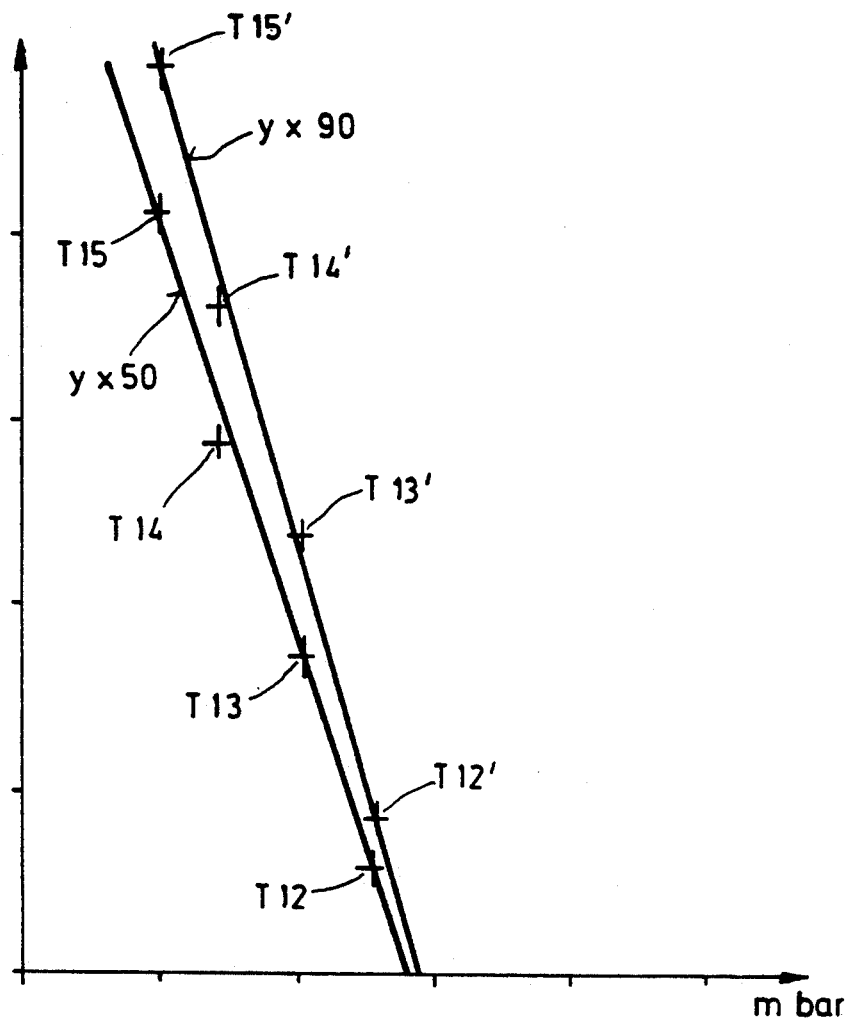
FIG. 5 represents a diagram for illustrating the particle size distribution of the examples according to the table described.

These samples were calculated by measuring the pressure drop with the help of an apparatus according to FIG. 4 due to various precompressions by piston 37, and their actual particle sizes determined in a customary way were then compared with these data. FIG. 5 shows that a linear correlation between the pressure drop x and the particle sizes for $y_{x50}$ and $y_{x90}$ results, with $y_{x50}$ representing a value corresponding to the average fineness, whereas $y_{x90}$ practically stands for a value corresponding to the maximum particle size. The table shows very well that the correlation factor R largely lies within a range of $-0.989$ and $-0.997$. In this connection, for the sake of good order, the correlation factor R (L) for the correlation between the grinding gap and the average ($\times 50$) and maximum (x90) particle sizes has been determined as well, lying within an order of 0.997 to 0.999.

The recalculation of the fineness takes place according to a linear regression equation $$y = m \cdot x + b,$$

in which
  y is the value to be determined for those particle size that corresponds to the average fineness ($y_{x50}$) or, approximately, to the maximum particle size ($y_{x90}$),
  m is a value that corresponds to the angle of climb of the straight lines for $y_{x50}$, or $y_{x90}$, respectively, in FIG. 5,
  x is the pressure drop in mbar; and
  b represents the value at the intersection of the straight lines $y_{x50}$, or $y_{x90}$, respectively, in FIG. 5, with the Y axis, that is, the distance of this intersection from the zero point.

It will be apparent that the angle of climb, that is, the value of m, will vary proportionally to the particle size ($y_{x50}$ or $y_{x90}$) on condition of a constant gas pressure when the sample in sample holder 24 is flown through. On the other hand, b will essentially depend on the kind of product inasmuch as at a constant slope (value m), the distance of the correlation line from the Y axis will determine the point of intersection with this latter. Of course, the calculation may also be made in other manners, but the one described above appears to be the most favorable one for practical purposes.

In principle, also non-linear regression equations may be used to get the desired result, but in this way, the correlation—as is clearly shown in FIG. 5—will largely be a linear one to such an extent that with the above method of calculation the object may be attained in a simplified way, which will also make it possible to simplify calculator 45.

Figure 6:
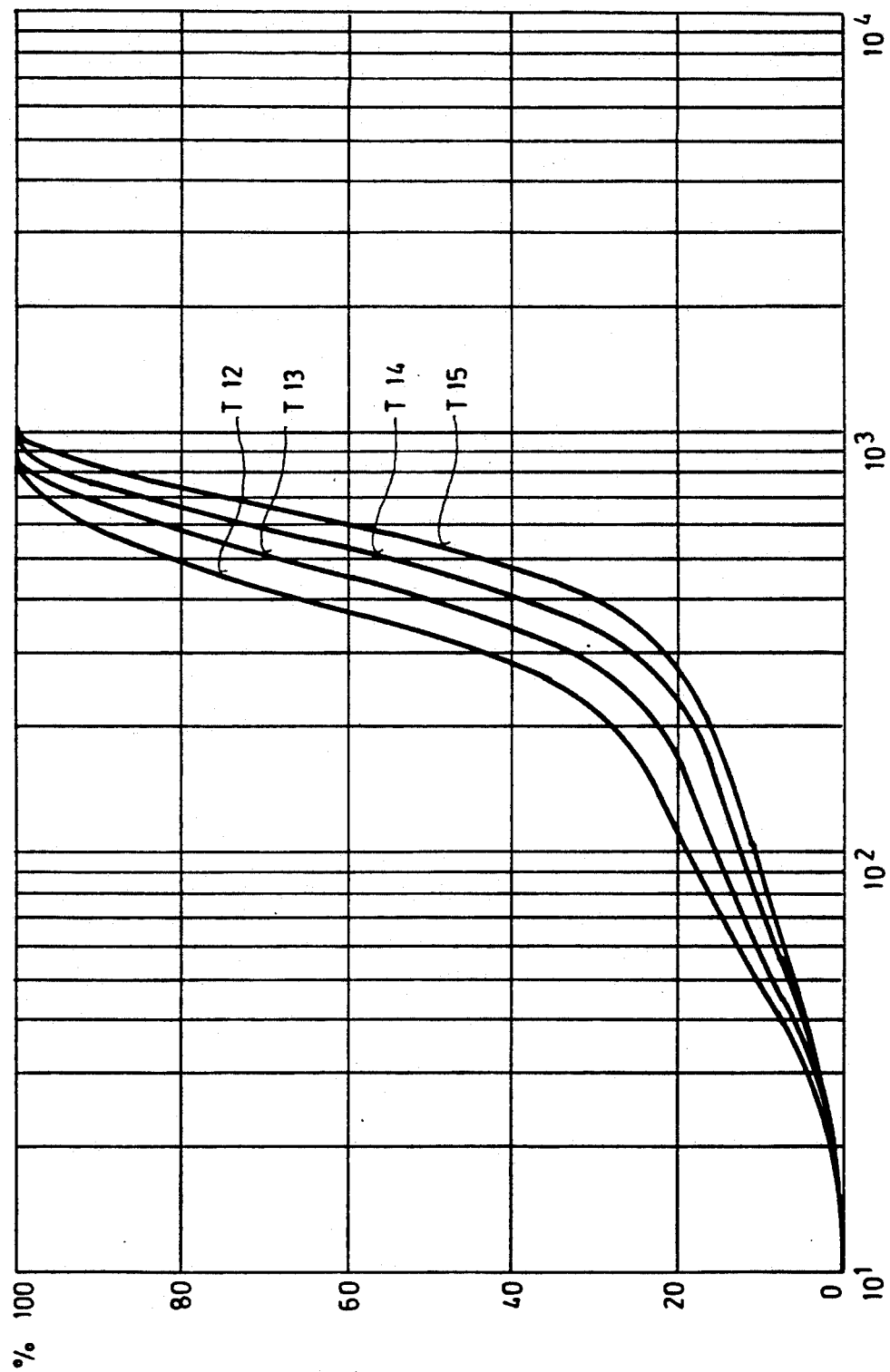
FIG. 6 shows the appertaining particle size distribution.

The particle size distribution of the four samples T12 to T15 is represented in FIG. 6, in which, on the vertical axis, the percentage figures are indicated, and, on the X axis the particle size in micron, so that with 50% the average fineness (measured with a customary method) can be determined and, with 90% approximately (not completely), the maximum particle size.

TABLE

| Sample No | grinding gap L (mm) | particle size (micron) | | pressure drop p (molar) with different compressions | | |
|---|---|---|---|---|---|---|
| | | x50 | x90 | F = 0 N | F = 250 N | F = 500 N |
| T 12 | 0.20 | 333 | 600 | 51 | 128 | 159 |
| T 13 | 0.24 | 403 | 690 | 41 | 96 | 118 |
| T 14 | 0.27 | 472 | 766 | 29 | 65 | 80 |
| T 15 | 0.30 | 546 | 845 | 21 | 48 | 55 |
| R (x90) | → | 0.997 | | −0.997 | −0.993 | −0.996 |
| R (x50) | | | 0.999 | −0.996 | −0.989 | −0.993 |
| R (L) | | | | | | |

Survey of the measured values and values of the linear progression equation y = m*x + b
R = correlation factor

What is claimed is:

1. A method for discontinuously determining the fineness of a continuously flowing bulk material by means of analysing samples being taken in intervals from said flowing bulk material comprising the steps of
   taking said samples of a predetermined volume at predetermined intervals from said flowing bulk material;
   forming samples of a substantially predetermined geometry.
   measuring flow parameters of said samples by making a stream of gas flowing through each of said samples, and
   deriving the fineness of said bulk material from said flow parameters.

2. Method as claimed in claim 1, wherein said fineness is determined after correcting the measured flow parameters by a value corresponding to the difference between an actual and a predetermined nominal sample geometry.

3. Method as claimed in claim 2, wherein each of said samples has a predetermined cross-sectional area and an actual height, said difference being that between said actual height and a predetermined nominal height.

4. Method as claimed in claim 1, further comprising the step of compressing said samples in a sample holder using a predetermined force.

5. Method as claimed in claim 4, wherein said force is applied by a piston compressor.

6. Method as claimed in claim 4, wherein said force is resulting from said bulk material being poured from a predetermined height into a sample holder.

7. Method as claimed in claim 1, further comprising the steps of
   weighing said sample to determined its weight;
   measuring the height of said sample;
   deriving a porosity value from said weight and height, forcing a gas through said sample;
   measuring the flow volume of said gas when passing at a certain gas pressure through said sample;
   deriving a gas flow resistance value from said flow volume and said gas pressure; and
   determining the particle size of said first bulk material from said derived values of said porosity and said gas flow resistance.

8. Method as claimed in claim 7, wherein said measuring of said sample height takes place after compressing said sample with a predetermined pressure force.

9. Method as claimed in claim 1, further comprising the steps of
   weighing said sample to determine its weight;
   measuring the height of said sample;
   deriving a porosity value from said weight and height,
   forcing a gas through said sample;
   measuring the flow volume of said gas when passing at a certain gas pressure through said sample;
   measuring the gas pressure drop due to the sample;
   deriving a gas flow resistance value from said gas flow volume and said gas pressure drop, and
   determining the particle size of said first bulk material from said derived values of said porosity and said gas flow resistance.

10. An apparatus for discontinuously determining the fineness of particles of a continuously flowing bulk material, comprising
    means for discontinuously taking samples from said continuously flowing bulk material;
    handling means for each of said samples, said handling means including
    sample holder means for successively receiving said samples;
    at least first and second handling stations for successively receiving said sample holder means, the sample holder being filled at said first station, while said sample is analysed at said second station by measuring at least one output value selected from the group of flow resistance of a stream of gas flowing through each of said samples, the pressure drop of said gas when flowing through said sample, volume and weight of each of said samples;
    computing means for calculating derived values selected from the group of fineness of said particles and bulk density from said output values using a predetermined algorithm.

11. Device as claimed in claim 10, further comprising an intermediate handling station between said first and second handling station, said intermediate handling station comprising piston means arranged for compressing said sample by displacement of it, and displacing means for said piston means.

12. Device as claimed in claim 10, wherein said second handling station comprises gas flow measuring means for measuring gas flow resistance properties of said sample.

13. Device as claimed in claim 12, wherein said sample holder has an open bottom side and wherein said gas flow means fit in a substantially gastight manner to said open bottom side of said sample holder.

14. Device as claimed in claim 10, wherein said sample holder has an open bottom side and wherein said handling means further comprise
   bottom plate means and
   transporting means for transporting said sample holder from one of said handling stations to the other, while said open bottom side stands on said bottom plate means.

15. Device as claimed in claim 10, wherein said second handling station comprises weighing means.

16. Device as claimed in claim 15, wherein said weighing means is the last one where said sample holder is transported to.

17. A grinding device for a bulk material comprising
   at least two grinding rolls forming a grinding gap between each other for grinding said bulk material when passing through said grinding gap,
   adjusting means for adjusting a desired gap by controlling at least one parameter determining said grinding gap,
   measuring means for measuring at least one property of said bulk material having passed through said grinding gap and for delivering an output value of said property,
   computing means receiving said output value and for calculating a value representing an actual fineness of said ground bulk material, and
   control means receiving said fineness value, comparing said fineness value with a predetermined nominal value, said control means being connected to said adjusting means.

18. Grinding device as claimed in claim 17, further comprising
   means for taking samples from said bulk material having passed through said grinding gap,
   handling means for each of said samples, said handling means including
      sample holder means for successively receiving said samples;
      at least first and second handling stations for successively receiving said sample holder means, the sample holder being filled at said first station, while said sample is analysed at said second station by measuring at least one output value selected from the group of flow resistance of a stream of gas flowing through each of said samples, the pressure drop of said gas when flowing through said sample, volume and weight of each of said samples.

19. Grinding device as claimed in claim 18, wherein said taking of samples is discontinuously effected.

20. Grinding device as claimed in claim 17, wherein said measuring means comprise means for measuring the permeability of said bulk material for adjusting said gap by said adjusting means.

21. Grinding device as claimed in claim 17, wherein said adjusting means comprise incremental driving means for adjusting said gap.

22. Grinding device as claimed in claim 21, further comprising displacement control means for controlling said incremental driving means at the beginning of its operation to bring said rolls into a predetermined position before forming said desired gap.

23. A grinding device for a bulk material comprising
   at least two grinding rolls,
   a grinding gap between said grinding rolls for grinding said bulk material when passing through said grinding gap,
   adjusting means for adjusting at least one parameter determining the density of said bulk material having passed through said grinding gap,
   means for taking a sample from said bulk material having passed through said grinding gap,
   first measuring means for measuring the volume of said sample,
   second measuring means for measuring the weight of said sample,
   computing means for inputting said volume and weight and for calculating an actual density value, and
   controlling means receiving said density value, comparing said actual density value with a predetermined nominal value and being connected to said adjusting means for maintaining the actual density value at least close to said nominal value.

24. Grinding device as claimed in claim 23, wherein said adjusting means are adjusting at least one parameter determining said grinding gap.

25. Grinding device as claimed in claim 23, wherein said adjusting means further comprise driving means for adjusting said gap.

26. Grinding device as claimed in claim 25, wherein said driving means are incremental driving means.

27. Grinding device as claimed in claim 26, wherein said incremental driving means need an initial offsetting by positioning said rolls at the beginning of operation at a predetermined position.

28. Grinding device as claimed in claim 23, further comprising
   compacting means arranged after said grinding rolls for exerting pressure to said bulk material being ground by passing through said grinding gap,
   said adjusting means comprising means for altering said pressure.

29. Grinding means as claimed in claim 28, wherein said pressure altering means comprise driving means for driving said compacting means.

30. Grinding device as claimed in claim 28, wherein said compacting means comprise a housing receiving the bulk material ground, and an outlet port formed on said housing, said pressure altering means comprising means for varying the cross-section of said outlet port.

31. Grinding device as claimed in claim 29, wherein said means for varying the cross-section of said outlet port comprise
   closing means movable between a closing position and an opening position, and
   second driving means for displacing said closing means.

32. A method according to claim 1, wherein said bulk material comprises flakes, and said measuring step provides for a measure of a side of the flakes, the method further comprising a step of adjusting the size of the flakes.

33. A method according to claim 1, wherein said bulk material comprises flakes, and said measuring step provides for a measure of a size of the flakes, the method further comprising a step of adjusting the size of the flakes.

34. An apparatus according to claim 10, wherein said bulk material comprises flakes, said computing means calculates a value of size of the flakes from data at said handling stations, and said apparatus further comprises means responsive to an output signal of the computer for altering a size of the flakes.

35. A grinding device according to claim 17, wherein said bulk material comprises flakes, and said one property of said bulk material is the size of the flakes.

36. A grinding device according to claim 23, wherein said bulk material comprises flakes, said grinding gap determining a density and a size of the flakes.

* * * * *